United States Patent
Dyballa et al.

(10) Patent No.: US 9,834,511 B2
(45) Date of Patent: Dec. 5, 2017

(54) ORGANODIARYL SELENOXIDES AND PROCESS FOR PREPARATION THEREOF

(71) Applicant: EVONIK DEGUSSA GMBH, Essen (DE)

(72) Inventors: Katrin Marie Dyballa, Recklinghausen (DE); Robert Franke, Marl (DE); Claudia Weilbeer, Bernburg (DE); Armin Börner, Rostock (DE); Detlef Selent, Rostock (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/371,593

(22) Filed: Dec. 7, 2016

(65) Prior Publication Data
US 2017/0158726 A1    Jun. 8, 2017

(30) Foreign Application Priority Data
Dec. 7, 2015 (EP) ..................................... 15198150

(51) Int. Cl.
| | | |
|---|---|---|
| *C07C 395/00* | (2006.01) | |
| *C07C 391/02* | (2006.01) | |
| *C07C 45/28* | (2006.01) | |
| *B01J 31/22* | (2006.01) | |
| *C07C 45/50* | (2006.01) | |
| *C07F 11/00* | (2006.01) | |
| *B01J 31/28* | (2006.01) | |
| *C07B 41/06* | (2006.01) | |
| *C07F 15/00* | (2006.01) | |

(52) U.S. Cl.
CPC .......... *C07C 391/02* (2013.01); *B01J 31/2208* (2013.01); *B01J 31/28* (2013.01); *C07B 41/06* (2013.01); *C07C 45/28* (2013.01); *C07C 45/50* (2013.01); *C07F 11/00* (2013.01); *C07F 11/005* (2013.01); *C07F 15/0073* (2013.01); *B01J 2231/321* (2013.01)

(58) Field of Classification Search
None
See application file for complete search history.

(56) References Cited

U.S. PATENT DOCUMENTS

| | | |
|---|---|---|
| 2015/0336865 A1 | 11/2015 | Dyballa et al. |
| 2015/0336885 A1 | 11/2015 | Dyballa et al. |
| 2015/0336995 A1 | 11/2015 | Dyballa et al. |

FOREIGN PATENT DOCUMENTS

| | | | |
|---|---|---|---|
| EP | 2949646 A1 | | 12/2015 |
| JP | 47035559 B | * | 9/1972 |
| WO | 2015/181018 A1 | | 12/2015 |
| WO | 2016/139245 A1 | | 9/2016 |

OTHER PUBLICATIONS

McCulla et al. J. Am. Chem. Soc. 2004, 126, 16058-16065.*
Wada et al., Journal of Organometallic Chemistry, 1999, 580(2) 282-289.*
Machine translation for JP-47035559.*
Search Report dated Feb. 16, 2017 for European Patent Application No. 16201606 (1 page).
Weilbeer et al. Evaluation of Organoselenium Based Compounds as Co-Catalysts in Rhodium-Catalyzed Hydroformylation. ChemistrySelect, 2016, 1. 5421-5429.
Paine et al. Manganese complexes of mixed O, X, O-donor ligands (X = S or Se): synthesis, characterization and catalytic reactivity, Dalton Trans., 2003, 3136-3144.
Lin et al. A novel and efficient synthesis of selenides. ARKIVOC, 2012, viii, 146-156.
Tricas et al. Bulky monophosphite ligands for ethene hydroformylation. Journal of Catalysis, 2013, 298, 198-205.
Franke, R., Selent, D., and Börner, A. Applied Hydroformylation. American Chemical Society, ACS Publications, Chemical Reviews, 2012. 5675-5732.

* cited by examiner

*Primary Examiner* — Sudhakar Katakam
*Assistant Examiner* — Ana Z Muresan
(74) *Attorney, Agent, or Firm* — Smith, Gambrell & Russell, LLP

(57) ABSTRACT

Novel organodiaryl selenoxides and processes for preparation thereof, and use thereof as ligand in complexes.

13 Claims, No Drawings

ORGANODIARYL SELENOXIDES AND PROCESS FOR PREPARATION THEREOF

Novel organodiaryl selenoxides and processes for preparation thereof, and use thereof as ligand in complexes.

The preparation of selenodiphenols unprotected on the hydroxyl group with low yields is known from T. K. Paine et al., "Manganese complexes of mixed O, X, O-donor ligands (X=S or Se): synthesis, characterization and catalytic reactivity", Dalton Trans., 2003, 15, 3136-3144). T. K. Paine et al. describes a synthesis of 2,2'-selenobis(4,6-di-tert-butylphenol) using selenium dioxide. The preparation of 2,2'-selenobis(4,6-di-tert-butylphenol) is effected here in an acidic medium with addition of concentrated hydrochloric acid. The product is obtained with a yield of only 25%.

A further multistage synthesis route using Grignard reagent is disclosed by H. M. Lin et al., "A novel and efficient synthesis of selenides", ARKIVOC, 2012, viii, 146-156. A synthetic route for selenobiaryl ethers is disclosed, in which bromine first has to be added onto the corresponding phenol in order to then react the product with magnesium to give a Grignard reagent. The Grignard reagent can then react with the added selenium before the actual coupling to give the biaryl ether:

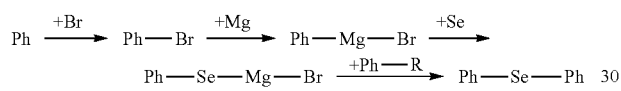

The product was obtained in a good yield, but this synthetic route is very complex, which makes it unattractive for industrial scale use. In this case, a multitude of synthetic steps are needed, the procedure for which is not uncritical in some cases, especially considering scale-up and using standards which are customary in industry. Moreover, this synthetic route gives rise to large amounts of waste products and solvents which have to be disposed of in a costly and inconvenient manner, one reason for which is the use of bromine.

EP 15168645.8 or U.S. Ser. No. 14/720,063 describes a large-scale economic synthetic route for preparing selenodiphenols.

The reactions between olefin compounds, carbon monoxide and hydrogen in the presence of a catalyst to give the aldehydes comprising one additional carbon atom are known as hydroformylation or oxidation. Catalysts used in these reactions are frequently compounds of the transition metals of group VIII of the Periodic Table of the Elements. Known ligands include, for example, compounds of the phosphine, phosphite and phosphonite classes each comprising trivalent phosphorus $P^{III}$. A good overview of the status of hydroformylation of olefins is found in R. Franke, D. Selent, A. Börner, "Applied Hydroformylation", Chem. Rev., 2012, DOI:10.1021/cr3001803.

Every catalytically active composition has its specific benefits. According to the feedstock and target product, therefore, different catalytically active compositions are used.

Rhodium-monophosphite complexes in catalytically active compositions are suitable for the hydroformylation of branched olefins having internal double bonds. Since the 1970s, there have been descriptions of the use of "bulky phosphites" in hydroformylation (see, inter alia, van Leeuwen et al., Journal of Catalysis, 2013, 298, 198-205). These feature good activity, but the n/i selectivity for terminally oxidized compounds is low and in need of improvement.

In these hydroformylations, monophosphites and bisphosphites are generally used, which are often formed from biphenol units. The development of novel ligands is frequently limited by the available biphenol, that is, ligand units. For instance, 2,2'-selenobiaryl ethers and also diphenyl selenoxides and diphenyl selenides represent a highly interesting class of compound. The 2,2'-selenobiaryl ethers are currently only being used in certain complexes, especially those containing manganese, but they have great potential for further uses.

The problem addressed by the invention was that of providing a further, wholly novel substance class of ligands and ligand units in order to broaden the field of available ligands for the respective specific complexes in catalysis. Another problem was that of preparing ligands for rhodium hydroformylation catalysts. Another problem was therefore that of providing novel intermediates as ligand units for preparation of ligands.

The problem is solved by organodiaryl selenoxides according to Claim 1. The invention thus provides at least one compound of an organodiaryl selenoxide having a general structure (Ia)

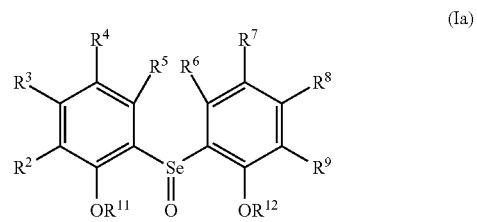

where $R^2$, $R^3$, $R^4$, $R^7$, $R^8$ and $R^9$ in structure (Ia) are each independently selected from: —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, —OC=O—$(C_1$-$C_{12})$-alkyl, —S-alkyl, —S-aryl, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —$SO_3H$, —CN, —N[$(C_1$-$C_{12})$-alkyl]$_2$, where the alkyl and aryl groups are each independently unsubstituted or substituted, where substituted —$(C_1$-$C_{12})$-alkyl groups and substituted —$(C_6$-$C_{20})$-aryl groups have at least one substituent and the at least one substituent is in each case independently selected from —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl, where $R^5$ and $R^6$ in structure (Ia) are each independently selected from: —H, —$(C_1$-$C_{12})$-alkyl, —O—$(C_2$-$C_{12})$-alkyl, —$(C_6$-$C_{20})$-aryl, —O—$(C_6$-$C_{20})$-aryl, -halogen, —OC=O—$(C_1$-$C_{12})$-alkyl, —S-alkyl, —S-aryl, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —$SO_3H$, —CN, —N[$(C_1$-$C_{12})$-alkyl]$_2$, where the alkyl and aryl groups are each independently unsubstituted or substituted, where substituted —$(C_1$-$C_{12})$-alkyl groups and substituted —$(C_6$-$C_{20})$-aryl groups have at least one substituent and the at least one substituent in each case is selected independently from —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl, where —$R^{11}$ and —$R^{13}$ in each case in structure (Ia) are independently selected from: —H, —$(C_1$-$C_{12})$-alkyl, —$(C_1$-$C_{12})$-alkyl-O—$(C_1$-$C_{12})$-alkyl, —$(C_6-C_{20})$-aryl, —$(C_1-C_{12})$-alkyl-O—$(C_6-C_{20})$-aryl, —$(C_6-C_{20})$-aryl-O—$(C_6-C_{20})$-aryl, —C=O—$(C_1-C_{12})$-alkyl, where the alkyl and aryl groups mentioned are each independently unsubstituted or substituted, where substituted —$(C_1-C_{12})$-alkyl groups and substituted —$(C_6-C_{20})$-aryl groups have at least one substituent and the at least one substituent is in each case independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl.

All elucidations relating to the expression —$(C_1-C_{12})$-alkyl also apply to the alkyl groups in —O—$(C_1-C_{12})$-alkyl, i.e. in —$(C_1-C_{12})$-alkoxy. Preferably, these groups are unsubstituted straight-chain or branched —$(C_1-C_6)$-alkoxy groups.

Substituted —$(C_1-C_{12})$-alkyl groups and substituted —$(C_1-C_{12})$-alkoxy groups may have one or more substituents, depending on their chain length. The substituents are preferably each independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl. This definition applies to all substituted alkyl or alkoxy groups of the present invention.

In the context of the present invention, the expression "—$(C_6-C_{20})$-aryl and —$(C_6-C_{20})$-aryl-$(C_6-C_{20})$-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —$(C_6-C_{10})$-aryl and —$(C_6-C_{10})$-aryl-$(C_6-C_{10})$-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

The expression "—$(C_3-C_{12})$-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl or adamantyl.

One example of a substituted cycloalkyl would be menthyl.

The expression "—$(C_3-C_{12})$-heterocycloalkyl groups", in the context of the present invention, encompasses nonaromatic, saturated or partly unsaturated cycloaliphatic groups having 3 to 12, especially 5 to 12, carbon atoms. The —$(C_3-C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— and —S(=O)—. Examples of —$(C_3-C_{12})$-heterocycloalkyl groups are tetrahydrothiophenyl, tetrahydrofuryl, tetrahydropyranyl and dioxanyl.

Halogen includes fluorine, chlorine, bromine and iodine, wherein particular preference is given to chlorine and fluorine.

An alkyl group according to the invention may in each case independently be linear, branched or cyclic.

One or more substituents comprise preferably 1 to 10 substituents, especially 1 to 3. In the context of the invention, the expression "—$(C_1-C_{12})$-alkyl" encompasses straight-chain and branched alkyl groups. Preferably, these groups are unsubstituted straight-chain or branched —$(C_1-C_8)$-alkyl groups and most preferably —$(C_1-C_6)$-alkyl groups. Examples of —$(C_1-C_{12})$-alkyl groups are particularly methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

In one alternative, $R^2$, $R^3$, $R^4$, $R^5$, $R^6$, $R^7$, $R^8$ and $R^9$ are each independently selected from: —H, —$(C_1-C_{12})$-alkyl, —O—$(C_1-C_{12})$-alkyl, —$(C_6-C_{20})$-aryl, —O—$(C_6-C_{20})$-aryl, -halogen.

In one alternative, $R^2$, $R^3$, $R^4$, $R^5$, $R^6$, $R^7$, $R^8$ and $R^9$ are each independently selected from: —H and —$(C_1-C_{12})$-alkyl.

In a particularly preferred embodiment, the organodiaryl selenoxide is selected from a compound having a general structure (Ib)

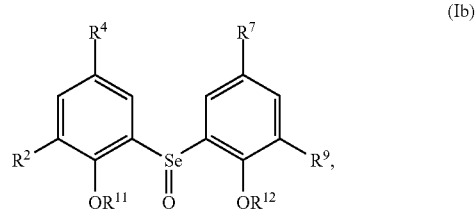

where $R^2$, $R^4$, $R^7$ and $R^9$ in structure (Ib) are —$(C_1-C_{12})$-alkyl, where —$R^{11}$ and —$R^{12}$ in each case in structure (Ib) are independently selected from: —H, —$(C_1-C_{12})$-alkyl, —$(C_1-C_{12})$-alkyl-O—$(C_1-C_{12})$-alkyl, —$(C_6-C_{20})$-aryl, —$(C_1-C_{12})$-alkyl-O—$(C_6-C_{20})$-aryl, —$(C_6-C_{20})$-aryl-O—$(C_6-C_{20})$-aryl, —C=O—$(C_1-C_{12})$-alkyl, where the alkyl and aryl groups mentioned are each independently unsubstituted or substituted, where substituted —$(C_1-C_{12})$-alkyl groups and substituted —$(C_8-C_{20})$-aryl groups have at least one substituent and the at least one substituent is in each case independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl.

In one embodiment, in the organodiaryl selenoxide of the structures (Ia), $R^2$, $R^3$, $R^4$, $R^7$, $R^8$ and $R^9$ are each independently selected from: —H, —$(C_1-C_{12})$-alkyl, —O—$(C_1-C_{12})$-alkyl, —$(C_6-C_{20})$-aryl, —O—$(C_6-C_{20})$-aryl, -halogen, —OC=O—$(C_1-C_{12})$-alkyl, —S-alkyl, —S-aryl, —COO—$(C_1-C_{12})$-alkyl, —CONH—$(C_1-C_{12})$-alkyl, —CO—$(C_1-C_{12})$-alkyl, —CO—$(C_6-C_{20})$-aryl, —COOH, —SO$_3$H, —CN, —N[$(C_1-C_{12})$-alkyl]$_2$, where the alkyl and aryl groups are each independently unsubstituted or substituted, where substituted —$(C_1-C_{12})$-alkyl groups and substituted —$(C_6-C_{20})$-aryl groups have at least one substituent and the at least one substituent is in each case independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl, and at least one radical of $R^2$, $R^3$, $R^4$, $R^7$, $R^8$ and $R^9$ is in each case independently selected from: —$(C_6-C_{20})$-aryl, —O—$(C_6-C_{20})$-aryl, -halogen, —OC=O—$(C_1-C_{12})$-alkyl, —S-alkyl, —S-aryl, —COO—

$(C_1-C_{12})$-alkyl, —CONH—$(C_1-C_{12})$-alkyl, —CO—$(C_1-C_{12})$-alkyl, —CO—$(C_6-C_{20})$-aryl, —COOH, —SO$_3$H, —CN, —N[$(C_1-C_{12})$-alkyl]$_2$,
where the alkyl and aryl groups are each independently unsubstituted or substituted, where substituted —$(C_1-C_{12})$-alkyl groups and substituted —$(C_6-C_{20})$-aryl groups have at least one substituent and the at least one substituent is in each case independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl.

In a preferred embodiment, $R^{11}$ and $R^{12}$ are the same. In addition, $R^{11}$ and $R^{12}$ are preferably the same and are selected from: -Me, —CH$_2$OCH$_3$ (MOM), —CH$_2$OCH$_2$C$_6$H$_5$ (BOM), —CH$_2$OCH$_2$CH$_2$OCH$_3$ (MEM), -benzyl (Bn).

Ether groups according to the invention are considered to be the oxygen-bridged groups —OR$^{11}$ and —OR$^{12}$ in which $R^{11}$ and $R^{12}$ are each independently selected from:
—$(C_1-C_{12})$-alkyl, —$(C_1-C_{12})$-alkyl-O—$(C_1-C_{12})$-alkyl, —$(C_6-C_{20})$-aryl,
—$(C_1-C_{12})$-alkyl-O—$(C_6-C_{20})$-aryl, —$(C_6-C_{20})$-aryl-O—$(C_6-C_{20})$-aryl.

More preferably, $R^{11}$ and $R^{12}$ in the structures Ia and Ib are each independently selected from: —H, methoxymethyl-, benzyl-, methyl-, tert-butyl.

In addition, $R^{11}$ and $R^{12}$ in the structures are each independently selected from: -Me, —CH$_2$OCH$_3$ (MOM), —CH$_2$OCH$_2$C$_6$H$_5$ (BOM), —CH$_2$OCH$_2$CH$_2$OCH$_3$ (MEM), benzyl-, it being further preferable when $R^{11}$ and $R^{12}$ are the same.

The invention likewise provides organodiaryl selenoxides of the structures Ia with $R^2$, $R^3$, $R^4$, $R^5$, $R^6$, $R^7$, $R^8$ and $R^9$ and Ib with $R^2$, $R^4$, $R^7$ and $R^9$ each independently selected from: —H, —$(C_1-C_{12})$-alkyl, —O—$(C_1-C_{12})$-alkyl, —$(C_6-C_{20})$-aryl, —O—$(C_6-C_{20})$-aryl, -halogen, —OC=O—$(C_1-C_{12})$-alkyl, —S-alkyl, —S-aryl, —COO—$(C_1-C_{12})$-alkyl, —CONH—$(C_1-C_{12})$-alkyl, —CO—$(C_1-C_{12})$-alkyl, —CO—$(C_6-C_{20})$-aryl, —COOH, —SO$_3$H, —CN, —N[$(C_1-C_{12})$-alkyl]$_2$, where the alkyl and aryl groups mentioned are each independently unsubstituted or substituted, where substituted —$(C_1-C_{12})$-alkyl groups and substituted —$(C_6-C_{20})$-aryl groups have at least one substituent and the at least one substituent in each case is independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl, where at least one radical of $R^2$, $R^3$, $R^4$, $R^5$, $R^6$, $R^7$, $R^8$ and $R^9$ in each case is independently selected from: —$(C_6-C_{20})$-aryl, —O—$(C_8-C_{20})$-aryl, -halogen, —OC=O—$(C_1-C_{12})$-alkyl, —S-alkyl, —S-aryl, —COO—$(C_6-C_{12})$-alkyl, —CONH—$(C_1-C_{12})$-alkyl, —CO—$(C_1-C_{12})$-alkyl, —CO—$(C_6-C_{20})$-aryl, —COOH, —SO$_3$H, —CN, —N[$(C_1-C_{12})$-alkyl]$_2$, where the alkyl and aryl groups are each independently unsubstituted or substituted, where substituted —$(C_1-C_{12})$-alkyl groups and substituted —$(C_6-C_{20})$-aryl groups have at least one substituent and the at least one substituent is each independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl, where, preferably, $R^{11}$ and $R^{12}$ are —H or $R^{11}$ and $R^{12}$ are —OH.

Preferably, at least one radical of $R^2$, $R^3$, $R^4$, $R^5$, $R^6$, $R^7$, $R^8$ and $R^9$ in each case is independently selected from: —$(C_6-C_{20})$-aryl, —O—$(C_6-C_{20})$-aryl, -halogen, and where a) $R^{11}$ and $R^{12}$ are —H or $R^{11}$ and $R^{12}$ are —OH or b) $R^{11}$ and $R^{12}$ are not the same when $R^{11}$ or $R^{12}$ is —H and $R^{11}$ and $R^{12}$ otherwise correspond to the general definition.

The invention further provides an organodiaryl selenoxide
wherein, in the organodiaryl selenoxide
a) of the structure (Ia) or (Ib), $R^{11}$ is the same as $R^{12}$ and is selected from methoxymethyl-, benzyl-, tert-butyl, or
b) of the structure (Ia) or (Ib), $R^{11}$ is selected from methoxymethyl-, benzyl-, tert-butyl, and $R^{12}$ is —H, or
c) of the structure (Ia) or (Ib), $R^{12}$ is selected from methoxymethyl-, benzyl-, tert-butyl, and $R^{11}$ is —H.

In one embodiment, $R^2$, $R^3$, $R^4$, $R^7$, $R^8$, $R^9$ are each independently selected from: —H, —$(C_1-C_{12})$-alkyl, —O—$(C_1-C_{12})$-alkyl, —$(C_6-C_{20})$-aryl and —O—$(C_6-C_{20})$-aryl.

In one embodiment, $R^5$ and $R^6$ are each independently selected from: —H, —$(C_1-C_{12})$-alkyl, —O—$(C_2-C_{12})$-alkyl, —$(C_6-C_{20})$-aryl and —O—$(C_6-C_{20})$-aryl.

In one embodiment, $R^2$, $R^4$, $R^7$, $R^9$ are each independently selected from: —$(C_1-C_{12})$-alkyl, —O—$(C_1-C_{12})$-alkyl, —$(C_6-C_{20})$-aryl and —O—$(C_6-C_{20})$-aryl.

In one embodiment, $R^2$, $R^4$, $R^7$, $R^9$ are each methyl- or tert-butyl- and $R^3$, $R^5$, $R^6$, $R^8$ are each —H.

In accordance with a further variant, the organodiaryl selenoxides of the structure Ia also include organodiphenyl selenoxides of the general structure Ib

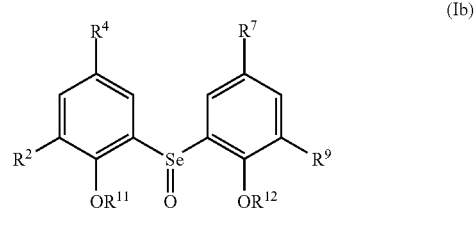

(Ib)

where $R^2$, $R^4$, $R^7$ and $R^9$ in structure Ib are each independently selected from: —$(C_1-C_{12})$-alkyl, —O—$(C_1-C_{12})$-alkyl, —$(C_6-C_{20})$-aryl, —O—$(C_6-C_{20})$-aryl, -halogen, where the alkyl and aryl groups mentioned are each independently unsubstituted or substituted, where substituted —$(C_1-C_{12})$-alkyl groups and substituted —$(C_6-C_{20})$-aryl groups have at least one substituent and the at least one substituent in each case is independently selected from —$(C_3-C_{12})$-cycloalkyl, —$(C_3-C_{12})$-heterocycloalkyl, —$(C_6-C_{20})$-aryl, and $R^3$, $R^5$, $R^6$ and $R^8$ are —H, and where, in structure Ib —$R^{11}$ and —$R^{12}$ are each —H. The organodiphenyl selenoxides of the structure Ib are preferably ligand units and hence intermediates for preparation of ligands, such as phosphite ligands.

In addition, in one variant, also include organodiphenyl selenoxides of the general structure Ic

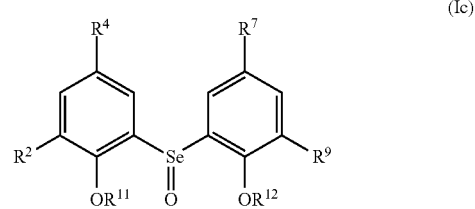

(Ic)

where $R^2$, $R^4$, $R^7$ and $R^9$ in structure Ic are each independently selected from: —$(C_1-C_{12})$-alkyl, —O—$(C_1-C_{12})$-alkyl, —$(C_6-C_{20})$-aryl, —O—$(C_6-C_{20})$-aryl, -halogen, and where, in structure Ic, —$R^{11}$ and —$R^{12}$ in structure (Ia) are each independently selected from:
—$(C_1$-$C_{12})$-alkyl, —$(C_1$-$C_{12})$-alkyl-O—$(C_1$-$C_{12})$-alkyl, —$(C_6$-$C_{20})$-aryl,
—$(C_1$-$C_{12})$-alkyl-O—$(C_6$-$C_{20})$-aryl, —$(C_6$-$C_{20})$-aryl-O—$(C_6$-$C_{20})$-aryl, where the alkyl and aryl groups mentioned are each independently unsubstituted.

The organodiphenyl selenoxides of the structure Ic are preferably ligands for preparation of complexes comprising at least one metal atom.

In accordance with a particularly preferred variant, $R^2$, $R^3$, $R^4$, $R^5$, $R^6$, $R^7$, $R^8$, $R^9$ in the organodiaryl selenoxides, especially the organodiphenyl selenoxides of the structures Ia, Ib, and/or Ic and in the organodiaryl selenides of the structure Il, are each independently selected from: —H, unsubstituted —$(C_1$-$C_{12})$-alkyl and/or unsubstituted —O—$(C_1$-$C_{12})$-alkyl groups, where the alkyl groups may be linear, branched or cyclic.

Particularly preferred ether-protected organodiphenyl selenoxides of the structure Ia and/or Ic, are the MOM-protected (methyloxymethyl) and Bn-protected (benzyl) organodiphenyl selenoxides of the structure Ic (1a with R=MOM, and 1b with R=Bn).

Further preferred organodiaryl selenoxides comprise structures Ia:
(i) where $R^2$, $R^3$, $R^4$, $R^5$, $R^6$, $R^7$, $R^8$, $R^9$ are each independently selected from: —H, —$(C_1$-$C_{12})$-alkyl, —O—$(C_1$-$C_{12})$-alkyl, —$(C_6$-$C_{20})$-aryl and —O—$(C_5$-$C_{20})$-aryl.
(ii) where $R^2$, $R^3$, $R^4$, $R^5$, $R^6$, $R^7$, $R^8$, $R^9$ are each independently selected from: —$(C_1$-$C_{12})$-alkyl, —O—$(C_1$-$C_{12})$-alkyl, —$(C_6$-$C_{20})$-aryl and —O—$(C_8$-$C_{20})$-aryl.
(iii) where $R^2$, $R^4$, $R^7$, $R^9$ are each independently selected from: —$(C_1$-$C_{12})$-alkyl, —O—$(C_1$-$C_{12})$-alkyl, —$(C_6$-$C_{20})$-aryl and —O—$(C_6$-$C_{20})$-aryl, especially of the structure Ib or Ic,
(iv) where $R^2$, $R^4$, $R^7$, $R^9$ are each methyl- or tert-butyl- and $R^3$, $R^5$, $R^6$, $R^8$ are each —H, where, in the alternatives (i), (ii), (iii) and (iv), $R^{11}$ and $R^{12}$ are preferably each independently selected from: -Me, —$CH_2OCH_3$ (MOM), —$CH_2OCH_2C_6H_5$ (BOM), —$CH_2OCH_2CH_2OCH_3$ (MEM), benzyl-, it being further preferable when $R^{11}$ and $R^{12}$ are the same.

The invention likewise provides a process for preparing an organodiaryl selenoxide of the general structure (Ia) comprising the process step of
(i) oxidizing an organodiaryl selenide of the general structure (IIa)

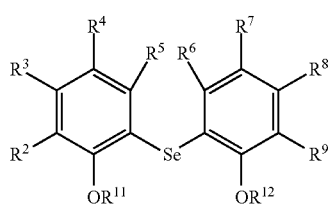

(IIa)

where $R^2$, $R^3$, $R^4$, $R^7$, $R^8$ and $R^9$ in structure (Ia) are each independently selected from: —H, —$(C_1$-$C_{12})$-alkyl, —O—$(C_1$-$C_{12})$-alkyl, —$(C_8$-$C_{20})$-aryl, —O—$(C_6$-$C_{20})$-aryl, -halogen, —OC=O—$(C_1$-$C_{12})$-alkyl, —S-alkyl, —S-aryl, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —$SO_3H$, —CN, —N[$(C_1$-$C_{12})$-alkyl]$_2$, where the alkyl and aryl groups are each independently unsubstituted or substituted, where substituted —$(C_1$-$C_{12})$-alkyl groups and substituted —$(C_6$-$C_{20})$-aryl groups have at least one substituent and the at least one substituent in each case is independently selected from —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl, where $R^5$ and $R^6$ in structure (Ia) are each independently selected from: —H, —$(C_1$-$C_{12})$-alkyl, —O—$(C_2$-$C_{12})$-alkyl, —$(C_6$-$C_{20})$-aryl, —O—$(C_6$-$C_{20})$-aryl, -halogen, —OC=O—$(C_1$-$C_{12})$-alkyl, —S-alkyl, —S-aryl, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —$SO_3H$, —CN, —N[$(C_1$-$C_{12})$-alkyl]$_2$, where the alkyl and aryl groups are each independently unsubstituted or substituted, where substituted —$(C_1$-$C_{12})$-alkyl groups and substituted —$(C_6$-$C_{20})$-aryl groups have at least one substituent and the at least one substituent in each case is independently selected from —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl, where —$R^{11}$ and —$R^{12}$ in structure (Ia) are each independently selected from: —H, —$(C_1$-$C_{12})$-alkyl, —$(C_1$-$C_{12})$-alkyl-O—$(C_1$-$C_{12})$-alkyl, —$(C_6$-$C_{20})$-aryl, —$(C_1$-$C_{12})$-alkyl-O—$(C_6$-$C_{20})$-aryl, —$(C_6$-$C_{20})$-aryl-O—$(C_6$-$C_{20})$-aryl, —(C=O)—O—$(C_1$-$C_{12})$-alkyl, where the alkyl and aryl groups mentioned are each independently unsubstituted or substituted, where substituted —$(C_1$-$C_{12})$-alkyl groups and substituted —$(C_6$-$C_{20})$-aryl groups have at least one substituent and the at least one substituent in each case is independently selected from —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl, (ii) at least one compound of an organodiaryl selenoxide of the general structure (Ia) is obtained

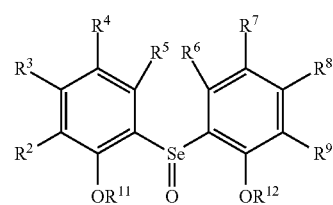

(Ia)

where $R^2$, $R^3$, $R^4$, $R^7$, $R^8$ and $R^9$ in structure (Ia) are each independently selected from: —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, —OC=O—$(C_1$-$C_{12})$-alkyl, —S-alkyl, —S-aryl, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —$SO_3H$, —CN, N[$(C_1$-$C_{12})$-alkyl]$_2$, where the alkyl and aryl groups are each independently unsubstituted or substituted, where substituted —$(C_1$-$C_{12})$-alkyl group and substituted —$(C_6$-$C_{20})$-aryl groups have at least one substituent and the at least one substituent is in each case independently selected from —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl, where $R^5$ and $R^6$ in structure (Ia) are each independently selected from: —H, —$(C_1$-$C_{12})$-alkyl, —O—$(C_2$-$C_{12})$-alkyl, —$(C_6$-$C_{20})$-aryl, —O—$(C_6$-$C_{20})$-aryl, -halogen, —OC=O—$(C_1$-$C_{12})$-alkyl, —S-alkyl, —S-aryl, —COO—$(C_1$-$C_{12})$-alkyl, —CONH—$(C_1$-$C_{12})$-alkyl, —CO—($C_1$-$C_{12}$)-alkyl, —CO—($C_6$-$C_{20}$)-aryl, —COOH, —$SO_3H$, —CN, N[($C_1$-$C_{12}$)-alkyl]$_2$, where the alkyl and aryl groups are each independently unsubstituted or substituted, where substituted —($C_1$-$C_{12}$)-alkyl group and substituted —($C_6$-$C_{20}$)-aryl groups have at least one substituent and the at least one substituent is in each case independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, where —$R^{11}$ and —$R^{12}$ in structure (Ia) are each independently selected from: —H, —($C_1$-$C_{12}$)-alkyl, —($C_1$-$C_{12}$)-alkyl-O—($C_1$-$C_{12}$)-alkyl, —($C_6$-$C_{20}$)-aryl, —($C_1$-$C_{12}$)-alkyl-O—($C_6$-$C_{20}$)-aryl, —($C_5$-$C_{20}$)-aryl-O—($C_6$-$C_{20}$)-aryl, —(C=O)—O—($C_1$-$C_{12}$)-alkyl, where the alkyl and aryl groups mentioned are each independently unsubstituted or substituted, where substituted —($C_1$-$C_{12}$)-alkyl groups and substituted —($C_6$-$C_{20}$)-aryl groups have at least one substituent and the at least one substituent in each case is independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl.

For (i) oxidation of the organodiaryl selenide of the general structure II it is possible with preference to use N-chlorosuccinimide (CNS), bromosuccinimide (BNS), hydrogen peroxide, tert-butyl hypochlorite (tBuOCl), sodium hypochlorite (NaOCl) and/or meta-chlorobenzoic acid (mCPBA). Particular preference is given to using N-chlorosuccinimide (CNS), bromosuccinimide (BNS) and especially N-chlorosuccinimide (CNS) for oxidation of the organodiaryl selenide of the structure II.

In accordance with a particularly preferred variant, $R^{11}$ and $R^{12}$ are each independently selected from: —($C_1$-$C_{12}$)-alkyl, —($C_1$-$C_{12}$)-alkyl-O—($C_1$-$C_{12}$)-alkyl, —($C_6$-$C_{20}$)-aryl, —($C_1$-$C_{12}$)-alkyl-O—($C_6$-$C_{20}$)-aryl, —($C_6$-$C_{20}$)-aryl-O—($C_6$-$C_{20}$)-aryl or $R^{11}$ or $R^{12}$ is —H and the other radical in each case from $R^{11}$ and $R^{12}$ is selected from: —($C_1$-$C_{12}$)-alkyl, —($C_1$-$C_{12}$)-alkyl-O—($C_1$-$C_{12}$)-alkyl, —($C_6$-$C_{20}$)-aryl, —($C_1$-$C_{12}$)-alkyl-O—($C_6$-$C_{20}$)-aryl, —($C_6$-$C_{20}$)-aryl-O—($C_6$-$C_{20}$)-aryl.

The invention likewise provides a process in which a diaryl selenide of the structure IIb or IIc is oxidized

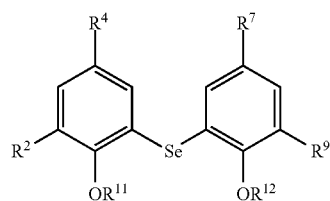

(IIb)

where $R^2$, $R^4$, $R^7$ and $R^9$ in structure IIb are each independently selected from: —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, where the alkyl and aryl groups mentioned are each independently unsubstituted or substituted, where substituted —($C_1$-$C_{12}$)-alkyl group and substituted —($C_6$-$C_{20}$)-aryl groups have at least one substituent and the at least one substituent is in each case independently selected from —($C_3$-$C_{12}$)-cycloalkyl, —($C_3$-$C_{12}$)-heterocycloalkyl, —($C_6$-$C_{20}$)-aryl, and $R^3$, $R^5$, $R^6$ and $R^8$ are —H and where, in structure IIb, —$R^{11}$ and —$R^{12}$ are each —H, and

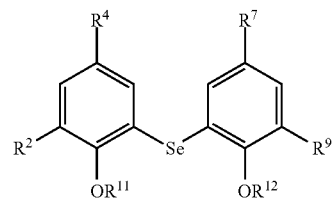

(IIc)

where $R^2$, $R^4$, $R^7$ and $R^9$ in structure IIc are each independently selected from: —($C_1$-$C_{12}$)alkyl, —O—($C_1$-$C_{12}$)-alkyl, —($C_6$-$C_{20}$)-aryl, —O—($C_6$-$C_{20}$)-aryl, -halogen, and $R^3$, $R^5$, $R^6$ and $R^8$ are —H and where, in structure IIc, —$R^{11}$ and —$R^{12}$ are each independently selected from: —($C_1$-$C_{12}$)-alkyl, —($C_1$-$C_{12}$)-alkyl-O—($C_1$-$C_{12}$)-alkyl, —($C_6$-$C_{20}$)-aryl, —($C_1$-$C_{12}$)-alkyl-O—($C_6$-$C_{20}$)-aryl, —($C_6$-$C_{20}$)-aryl-O—($C_6$-$C_{20}$)-aryl, where the alkyl and aryl groups mentioned are each independently unsubstituted, as defined above.

The invention further provides a complex comprising
at least one organodiaryl selenoxide as described above and
at least one metal atom selected from Rh, Ru, Co, Ir.

In a further embodiment, the invention provides a complex comprising at least one compound of the general structure Ic and at least one metal atom selected from Rh, Ru, Co, Ir, especially Rh, Ir, Ru, preferably Rh. In this context, the complexes preferably comprise the structure Ic where $R^{11}$ is —$OR^{11}$ and $R^{12}$ is —$OR^{12}$, where $R^{11}$ and $R^{12}$ are not —H and $R^{11}$ and $R^{12}$ otherwise correspond to the aforementioned definitions, preferably where $R^{11}$ is the same as $R^{12}$.

The invention further provides for the use of at least one compound as described previously
a) as ligand in a complex comprising at least one metal atom or
b) for catalysis of a hydroformylation reaction.

The invention further provides for the use of an organodiaryl selenoxide of the structure Ic or of mixtures comprising at least two of the structures mentioned in which $R^{11}$ and $R^{12}$ are not —H and where $R^{11}$ and $R^{12}$ otherwise correspond to the aforementioned definitions, preferably where $R^{11}$ is the same as $R^{12}$, as ligand in a complex comprising at least one metal atom, preferably selected from Rh, Ru, Co, Ir, especially Rh, Ir, Ru, preferably Rh.

In a further alternative, the invention provides for the use of at least one compound of the general structure Ic or of mixtures comprising at least two of the structures mentioned for catalysis of a hydroformylation reaction, particular preference being given to the use of a compound of the structure Ic in which $R^{11}$ and $R^{12}$ are not —H and $R^{11}$ and $R^{12}$ otherwise correspond to the aforementioned definitions, preferably where $R^{11}$ is the same as $R^{12}$.

The invention further provides a process comprising the steps of
(i) initially charging at least one olefin,
(ii) adding a complex comprising at least one organodiaryl selenoxide of the general structure Ic and at least one metal atom selected from Rh, Ru, Co, Ir, especially Rh, Ir, Ru, preferably Rh, and/or an organodiaryl selenoxide of the general structure Ic, and a substance including a metal atom selected from Rh, Ru, Co, Ir, especially Rh, Ir, Ru, preferably Rh
(iii) feeding in $H_2$ and CO,
(iv) heating the reaction mixture, wherein the olefin is converted to an aldehyde. The method steps (i), (ii), (iii) and (iv) can alternatively be carried out in any sequence.

It is preferably possible with the inventive compounds of the structures Ic, in a hydroformylation according to the above use or above process, to achieve a yield of not less than 80%, especially greater than 85%, preferably greater than 90%, and/or an n-regioselectivity of greater than 15%, especially greater than 20%.

The invention is further illustrated in detail below by examples without the invention being limited to the working examples.

GENERAL METHODS

Solvents and Reagents

All reactions with moisture- and/or oxygen-sensitive substances were carried out in baked-out apparatuses under an argon atmosphere. Solvents for extraction and column chromatography were used at the following purities: dichloromethane (99.9%, Walter, Cat. No. BIE 073107033) ethyl acetate (99.5%, Walter, Cat. No. BIE 003917025) and n-hexane (95%, Walter (Baker), Cat. No. 8669). n-heptane (95%, Walter (Baker), Cat. No. 8662). Other solvents for extraction and column chromatography were of technical quality and were used without further purification unless otherwise stated. Dry solvents (abs.) were purified using a Pure Solv MD-7 System and stored under an argon atmosphere. Benzyl bromide was freshly distilled (17 mbar/82° C.) prior to use. Deuterated solvents were distilled from the drying agents specified: dichloromethane-$d_2$ (phosphorus pentoxide), toluene-$d_8$ (1. KOH; 2. sodium). Chemicals used for the syntheses were supplied by Sigma Aldrich, Alfa Aesar, Acros Organics, Avantor Performance Materials B.V., Merck KGaA and ABCR GmbH & Co. KG. These were used without further purification unless otherwise stated.

Chromatographic Methods

Column chromatography: Column chromatographic separations were carried out at elevated pressure (flash chromatography) on silica gel 60 230-400 mesh from Merck KGaA (particle size: 0.040-0.063 mm). The eluent mixtures used and the ratios by volume v/v are indicated in the specifications below. The following abbreviations apply to the eluents used: DCM (dichloromethane), EA (ethyl acetate), H (n-hexane) and Tol (toluene).

Filtration: Filtrations for the removal of resulting solids were carried out using a G4 frit (pore width: 10-16 μm).

Analysis

IR spectroscopy: IR spectra were recorded with a Nicolet 6700 FT-IR spectrometer from Thermo Electron. The substances were measured by ATR methods.

$^1$H NMR spectroscopy: $^1$H NMR spectra were recorded with a model AV 300 (300 MHz) and with the model Fourier 300 (300 MHz) from Bruker. Chemical shifts are stated in units on the δ-scale. The residual proton signals of the solvent (dichloromethane-$d_2$: δ=5.32 ppm, toluene-$d_8$: δ=7.09; 7.00; 6.98; 2.09 ppm) served as standard.

$^{13}$C NMR spectroscopy: $^{13}$C NMR spectra were recorded with models AV 300 (75 MHz) and Fourier 300 (75 MHz) from Bruker. The signal of the solvent (dichloromethane-$d_2$: δ=54.0 ppm, toluene-$d_8$: δ=137.9; 129.2; 128.3; 125.5; 20.4 ppm) served as internal standard wherein the chemical shifts were taken from the broadband $^1$H-decoupled spectra.

$^{77}$Se NMR spectroscopy: $^{77}$Se-NMR spectra were recorded with an AV 300 (57 MHz) from Bruker. The spectra were measured in broadband $^1$H-decoupled mode. The chemical shifts are reported in ppm.

Mass spectrometry: EI mass spectra were recorded on a Finnigan MAT 95-XP instrument from Thermo Electron and ESI-TOF mass spectra with a model 6210 Time-of-Flight LC/MS from Agilent.

Autoclave Experiments of Rhodium-catalyzed Hydroformylation

The hydroformylation was conducted in a 200 ml autoclave equipped with pressure-retaining valve, gas flow meter, sparging stirrer and pressure pipette from Premex Reactor AG, Lengau, Switzerland. The toluene used as solvent was purified using a Pure Solv MD-7 System and stored under argon. The 1-octene or n-octenes substrate (EVONIK Industries AG, octene isomer mixture of 1-octene: 3.3%; cis+trans-2-octene: 48.5%; cis+trans-3-octene: 29.2%; cis+trans-octene-4: 16.4%; structurally isomeric octenes: 2.6%) used as substrate was heated at reflux over sodium for several hours and distilled under argon.

For the experiments, solutions of the catalyst precursor and the ligand were mixed in the autoclave under an argon atmosphere. [(acac)Rh(COD)] (Umicore, acac=acetylacetonate anion; COD=1,5-cyclooctadiene) was used as catalyst precursor. For experiments at a concentration of 100 ppm-m rhodium, 10 ml of a 4.31 mM solution was placed in the autoclave. Subsequently, the mass of ligand corresponding to a ratio L/Rh=5:1 (or 1:1) was dissolved and mixed in 10 ml of toluene. By adding further toluene, the starting volume of the catalyst solution was adjusted to 41.0 ml. Into a pressure-resistant pipette was filled: 1-octene or n-octenes (10.70 g). The autoclave was heated to the temperatures stated in each case at a total gas pressure (synthesis gas: Linde; $H_2$ (99.999%): CO (99.997%)=1:1) of a) 42 bar for a final pressure of 50 bar or b) 12 bar for a final pressure of 20 bar with stirring (1500 rpm). After reaching the reaction temperature, the synthesis gas pressure was increased to a) 48.5 bar for a final pressure of 50 bar or b) 19.5 bar for a final pressure of 20 bar and the reactant was introduced under a positive pressure of about 3 bar set in the pressure pipette. The reaction was conducted at a constant pressure of 50 or 20 bar (closed-loop pressure controller from Bronkhorst, the Netherlands) respectively over 4 h. After the reaction time had elapsed, the autoclave was cooled to room temperature, decompressed while stirring and purged with argon. 1.0 ml of each reaction mixture was removed immediately after the stirrer had been switched off, diluted with 5.0 ml of pentane and analyzed by gas chromatography: HP 5890 Series II plus, PONA, 50 m×0.2 mm×0.5 μm.

Abbreviations: Bn=Benzyl; calc.=calculated; MOM=methylmethoxy; NCS=N-chlorosuccinimide; RT=room temperature General Procedure for Synthesis of the Precursors:

General Procedure (GP1) for Preparation of Organodiaryl Selenides II as Selenodiphenols The appropriate phenols (1 equivalent) were added to a mixture of selenoxide (0.6 equivalent) in pyridine and stirred at 55-85° C. for 2-18 hours. Subsequently, the reaction mixtures were diluted with ethyl acetate and filtered, and the organic phases were washed with hydrochloric acid (10%) and water. After the organic phase had been removed, it was dried over magnesium sulphate and the solvent was distilled off under reduced pressure. The crude product of II was purified by column chromatography in each case.

Bis(3,5-dimethyl-2-hydroxyphenyl)selenium, IIb (1)

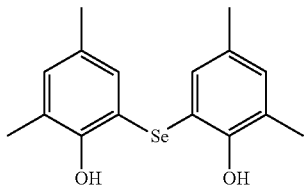

In a 250 ml round-bottom flask, 49.9 g of selenium dioxide (413 mmol) in 100 ml of pyridine were heated to 55° C. with the aid of an oil bath. Subsequently, 25 ml of 2,4-dimethylphenol (206 mmol) were added and the temperature was maintained for seven-and-a-half hours. On completion of the reaction, the mixture was diluted with 400 ml of ethyl acetate and filtered. The organic phase was washed with water and dried over magnesium sulphate. The pyridine was removed by distillation and the residue redissolved in ethyl acetate and washed with 10% hydrochloric acid and water in order to remove residues of pyridine. The organic phase was dried over magnesium sulphate and freed of the solvent under reduced pressure. The crude product thus obtained was heated under reflux in 400 ml of cyclohexane. After cooling to room temperature, the product crystallized. After one day, the product was filtered off, the filtrate was concentrated by half and again brought to crystallization at 4° C. 18.56 g, 58 mmol (56%) of fine, pale yellow flakes of the product were obtained.

$m_p$=120.1° C. (recrystallization from cyclohexane)
$^1$H NMR (400 MHz, CDCl$_3$) δ=7.11-7.12 (m, 2H), 6.90-6.92 (m, 2H), 5.95 (br, 2H, OH), 2.23 (s, 6H), 2.19 (s, 6H); $^{13}$C NMR (100 MHz, CDCl$_3$) δ=152.04, 133.35, 133.30, 130.67, 124.42, 115.31, 20.45, 16.69; $^{77}$Se NMR (76 MHz, CDCl$_3$) δ=164.91; HRMS for C$_{16}$H$_{18}$O$_2^{80}$Se (ESI+) [M+Na$^+$]: calculated: 345.0370, found: 445.0363;

Elemental analysis for C$_{16}$H$_{18}$O$_2$Se: calculated: C: 59.82%, H: 5.65%, found: C: 59.69%, H: 5.76%.

Di-(3-tert-butyl-2-hydroxy-5-methylphenyl)selenium, IIb (2)

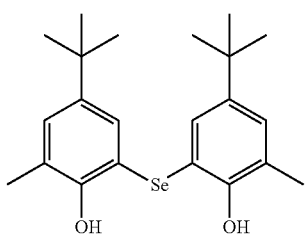

As described in GP1, 0.80 g of 4-tert-butyl-2-methylphenol (4.9 mmol, 1.0 eq.) was added to a solution of 0.33 g of selenium dioxide (2.9 mmol, 0.6 eq.) in 6.7 ml of pyridine and the mixture was stirred at 55° C. for 56 hours. The reaction mixture was diluted with 50 ml of ethyl acetate and filtered, and washed three times with 50 ml each time of hydrochloric acid (10%) and once with 50 ml of sodium chloride solution. After drying over magnesium sulphate, the solvent was removed under reduced pressure and the residue obtained was purified by column chromatography (eluent: cyclohexane/ethyl acetate 99:1). Yield: 36%, 0.35 g, 0.9 mmol.

$m_p$=98.5° C.; $^1$H NMR (400 MHz, CDCl$_3$) δ=7.30 (d, $^4$J=2.4 Hz, 2H), 7.11 (d, $^4$J=2.4 Hz, 2H), 5.92 (s, 2H, OH), 2.26 (d, 6H), 1.23 (s, 18H); $^{13}$C NMR (100 MHz, CDCl$_3$) δ=151.78, 144.03, 129.83, 129.51, 123.89, 114.95, 34.18, 31.56, 16.99; HRMS for C$_{22}$H$_{30}$O$_2^{80}$Se (ESI+) [M+Na$^+$]: calculated: 429.1309, found: 429.1250.

Bis(3,5-di-tert-butyl-2-hydroxyphenyl)selenium, IIb (3)

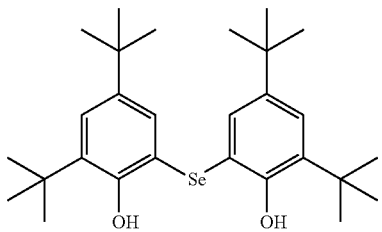 [SMILES: CC(C)(C)c1cc([Se]c2cc(C(C)(C)C)cc(C(C)(C)C)c2O)c(O)c(C(C)(C)C)c1]

As described in GP1, 0.80 g of 2,4-di-tert-butylphenol (3.8 mmol, 1.0 eq.) was added to a solution of 0.25 g of selenium dioxide (2.3 mmol, 0.6 eq.) in 5.4 ml of pyridine and the mixture was stirred at 55° C. for 4 days. The reaction mixture was diluted with 50 ml of ethyl acetate and filtered, and washed three times with 50 ml each time of hydrochloric acid (10%) and once with 50 ml of sodium chloride solution. After drying over magnesium sulphate, the solvent was removed under reduced pressure and the residue obtained was purified by column chromatography (eluent: cyclohexane/ethyl acetate 99:1). The desired product was crystallized out of n-heptane at 4° C. Yield: 25%, 0.24 g, 0.5 mmol.

$m_p$=141.1° C. (recrystallization from heptane); $^1$H NMR (400 MHz, CDCl$_3$) δ=7.31 (d, $^4$J=2.4 Hz, 2H), 7.29 (d, $^4$J=2.4 Hz, 2H), 6.29 (s, 2H, OH), 1.42 (s, 18H), 1.24 (s, 18H);

$^{13}$C NMR (100 MHz, CDCl$_3$) δ=151.7, 143.5, 135.8, 129.8, 125.6, 117.2, 35.4, 34.4, 31.6, 29.7; HRMS for C$_{28}$H$_{42}$O$_2^{80}$Se (ESI+) [M+Na$^+$]: calculated: 513.2248, found: 513.2152.

Di(3-tert-butyl-5-ethyl-2-hydroxyphenyl)selenium, IIb (4)

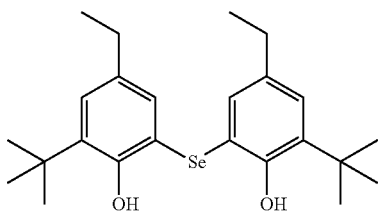 [SMILES: CCc1cc([Se]c2cc(CC)cc(C(C)(C)C)c2O)c(O)c(C(C)(C)C)c1]

As described in GP1, 2.00 g of 2-tert-butyl-4-ethylphenol (15.8 mmol, 1.0 eq.) was added to a solution of 1.06 g of selenium dioxide (9.5 mmol, 0.6 eq.) in 18 ml of pyridine and the mixture was stirred at 60° C. for 4 days. The reaction mixture was diluted with 50 ml of ethyl acetate and filtered, and washed three times with 50 ml each time of hydrochloric acid (10%) and once with 50 ml of sodium chloride solution. After drying over magnesium sulphate, the solvent was removed under reduced pressure and the residue obtained was purified by column chromatography (eluent: cyclohexane/ethyl acetate 99:1). Yield: 27%, 0.659 g, 1.5 mmol.

$m_p$=68.2° C.; $^1$H NMR (400 MHz, CDCl$_3$) δ=7.18 (d, $^4$J=2.1 Hz, 2H), 7.07 (d, $^4$J=2.1 Hz, 2H), 6.32 (s, 2H, OH), 2.51 (q, $^3$J=7.6 Hz, 4H), 1.40 (s, 18H), 1.16 (t, $^3$J=7.6 Hz, 6H).

$^{13}$C NMR (100 MHz, CDCl$_3$) δ=152.00, 136.42, 136.32, 131.98, 128.22, 117.19, 35.09, 29.53, 28.12, 15.66; HRMS for $C_{24}H_{24}O_2{}^{80}Se$ (ESI+) [M+Na$^+$]: calculated: 457.1622, found: 457.1632; elemental analysis for $C_{24}H_{24}O_2Se$: calculated: C: 66.50%, H: 7.38%, found: C: 66.26%, H: 7.54%.

Bis(3,5-di(1,1-dimethylpropyl)-2-hydroxyphenyl)selenium, IIb (5)

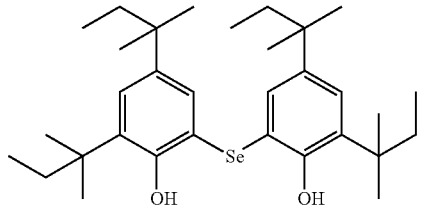 [SMILES: CCC(C)(C)c1cc([Se]c2cc(C(C)(C)CC)cc(C(C)(C)CC)c2O)c(O)c(C(C)(C)CC)c1]

As described in GP1, 2.00 g of 2,4-di(1,1-dimethylpropyl)phenol (13.6 mmol, 1.0 eq.) was added to a solution of 0.91 g of selenium dioxide (8.2 mmol, 0.6 eq.) in 19 ml of pyridine and the mixture was stirred at 60° C. for 4 days. The reaction mixture was diluted with 50 ml of ethyl acetate and filtered, and washed three times with 50 ml each time of hydrochloric acid (10%) and once with 50 ml of sodium chloride solution. After drying over magnesium sulphate, the solvent was removed under reduced pressure and the residue obtained was purified by column chromatography (eluent: cyclohexane/ethyl acetate with a gradient from 100:0 to 95:5). Yield: 25%, 0.586 g, 1.1 mmol.

$m_p$=119.7° C.; $^1$H NMR (400 MHz, CDCl$_3$) δ=7.18 (d, $^4$J=2.3 Hz, 2H), 7.11 (d, $^4$J=2.3 Hz, 2H), 6.15 (s, 2H), 1.82 (q, $^3$J=7.5 Hz, 4 H), 1.50 (q, $^3$J=7.4 Hz, 4 H), 1.34 (s, 12H), 1.16 (s, 12H), 0.58 (q, $^3$J=7.5 Hz, 12 H); $^{13}$C NMR (100 MHz, CDCl$_3$) δ=151.34, 142.32, 133.78, 130.15, 127.34, 116.99, 38.85, 37.45, 36.94, 33.11, 28.45, 27.72, 9.46, 9.01; HRMS for $C_{22}H_{30}O_2{}^{80}Se$ (ESI+) [M+Na$^+$]: calculated: 569.2874, found: 569.2800.

Synthesis of the Hydroxyl-Protected Selenodiphenols IIc (1a, 1b)

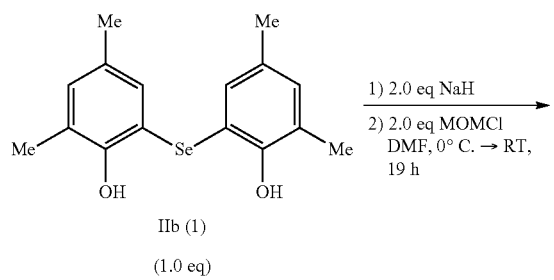

IIb (1)
(1.0 eq)

1) 2.0 eq NaH
2) 2.0 eq MOMCl
DMF, 0° C. → RT,
19 h

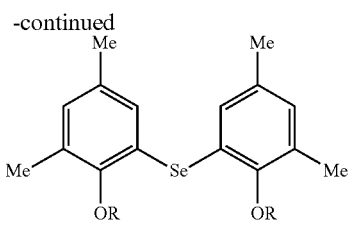

IIc

R = MOM: IIc (1a), Bn: IIc (1b)

EXAMPLE 1

In a baked-out 25 ml Schlenk flask under an argon atmosphere, 2.0 eq of sodium hydride (60% in paraffin oil) were suspended in 3.0 ml of abs. DMF and cooled to 0° C. Subsequently, 1.0 eq of selenodiphenol IIb, dissolved in 2.0 ml of abs, DMF, was added dropwise. The resulting yellowish solution was stirred at 0° C. for 10 minutes and at RT for one hour. Subsequently, another 2.0 eq. of the halide were added at 0° C. and the mixture was stirred at 0° C. for 10 minutes, in the course of which cloudiness of the reaction mixture was observed. After a further 17 hours at RT, while cooling with ice, water (3.0 ml/1.0 mmol) was added and the resultant phases were separated. The aqueous phase was extracted with ethyl acetate (3×5.0 ml/1.0 mmol). The combined organic phases were washed with water (2×10 ml/1.0 mmol) and a saturated NaCl solution (2×10 ml/1.0 mmol) and dried over magnesium sulphate. The desiccant was filtered off and the solvent was removed under reduced pressure. The yellowish oil obtained was taken up in acetonitrile (5.0 ml/1.0 mmol) and admixed with n-heptane (2.5 ml/1.0 mmol). The phases were separated and the solvent was removed under reduced pressure. The crude product was dried at 50° C. under reduced pressure for three hours.

EXAMPLE 2

Synthesis of bis(2-(methoxymethoxy)-3,5-dimethylphenyl)selane IIc (1a)

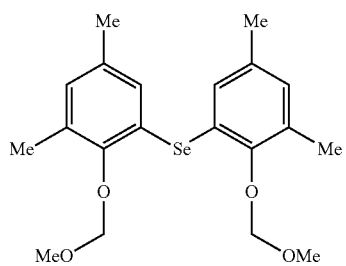 [SMILES: COCOc1c(C)cc(C)cc1[Se]c1cc(C)cc(C)c1OCOC]

According to Example 1, 81.0 mg (2.03 mmol, 2.0 eq, 60% in paraffin oil) of sodium hydride and 548 mg (1.70 mmol, 1.0 eq) of selenodiphenol IIb were reacted with 153 μl (301 mg, 3.74 mmol, 2.0 eq) of chlorodimethyl ether. After extractive workup, 657 mg (1.60 mmol, 94%) of the title compound IIc (1a) were obtained as a pale yellow oil.

IR (ATR): ῦ (cm$^{-1}$)=2922; 2824; 2772; 1739; 1598; 1568; 1471; 1432; 1395; 1270; 1226; 1194; 1154; 1126; 1069; 951; 924; 849; 814; 796; 757; 727; 581; 540; 511; 477; 440;

¹H NMR (300 MHz, dichloromethane-d₂): δ (ppm)=6.85 (dp, J=2.2 Hz, J=0.7 Hz, 2H, Ar—CH); 6.75 (dp, J=2.2 Hz, J=0.7 Hz, 2H, Ar—CH); 4.92 (s, 4H, —OCH₂CH₃); 3.50 (s, 6H, —OCH₃); 2.22 (t, J=0.7 Hz, 6H, —CH₃); 2.09 (t, J=0.7 Hz, 6H, —CH₃); ¹³C NMR (75 MHz, dichloromethane-d₂): δ (ppm)=153.4; 135.2; 132.5; 132.1; 131.9; 125.0; 100.0; 57.85; 20.69; 17.25; ⁷⁷Se NMR (57 MHz, dichloromethane-d₂): δ (ppm)=309.0; HR-MS (ESI-TOF): calc. for C₂₀H₂₆O₄SeNa ([M+Na]⁺): 433.08896, found: 433.08876; C₂₀H₂₆O₄Se (410.10 g/mol).

EXAMPLE 3

Synthesis of bis(2-(benzyloxy)-3,5-dimethylphenyl)selane IIc (1b)

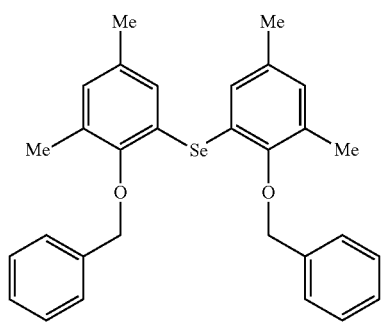 [SMILES: Cc1cc(C)c(OCc2ccccc2)c([Se]c2cc(C)cc(C)c2OCc2ccccc2)c1]

According to Example 1, 82.4 mg (2.06 mmol, 2.0 eq, 60% in paraffin oil) of sodium hydride and 331 mg (1.03 mmol, 1.0 eq) of selenodiphenol IIb were reacted with 244 µl (352 mg, 2.06 mmol, 2.0 eq) of benzyl bromide. After extractive workup, 407 mg (0.810 mmol, 79%) of the title compound IIc (1b) were obtained as a pale yellow oil.

IR (ATR): ν̂ (cm⁻¹)=3088; 3063; 3029; 2917; 2859; 2730; 1598; 1566; 1497; 1465; 1453; 1370; 1308; 1270; 1209; 1127; 1078; 978; 912; 848; 815; 776; 749; 725; 694; 601; 569; 513; 492; 466; ¹H NMR (300 MHz, dichloromethane-d₂): δ (ppm)=7.42-7.30 (m, 4H, Ar—CH); 7.30-7.09 (m, 6H, Ar—CH); 6.90-6.68 (m, 4H, Ar—CH); 4.78 (s, 4H, —OCH₂Ph); 2.19 (s, 6H, —CH₃); 2.10 (t, J=0.7 Hz, 6H, —CH₃); ¹³C NMR (75 MHz, dichloromethane-d₂): δ (ppm)=154.5; 138.0; 135.2; 132.6; 132.0; 131.9; 128.7; 128.5; 128.3; 125.1; 74.77; 20.86; 1677; ⁷⁷Se-NMR (57 MHz, dichloromethane-d₂): δ (ppm)=299.2; ⁷⁷Se-NMR (57 MHz, toluene-d₈): δ (ppm)=302.6; MS (ESI-TOF): m/z=525.130 ([M+Na]⁺); 541.124 ([M+K]⁺); HR-MS (ESI-TOF): calc. for C₃₀H₃₀O₂SeNa ([M+Na]⁺); 525.13053, found: 525.12986; C₃₀H₃₀O₂Se (502.14 g/mol).

Both bis(3,5-dimethyl-2-hydroxyphenyl)selenium, di-(3-tert-butyl-2-hydroxy-5-methyl-phenyl)selenium; bis(3,5-di-tert-butyl-2-hydroxyphenyl)selenium; di(3-tert-butyl-5-ethyl-2-hydroxyphenyl)selenium; bis(3,5-di(1,1-dimethylpropyl)-2-hydroxyphenyl)selenium; bis(3-tert-butyl-5-methyl-2-hydroxyphenyl)selenium, bis(3,3',5,5'-tetra-tert-butyl-2-hydroxyphenyl)selenium can be converted analogously to Examples 1 to 3 to the corresponding bis(2-(methoxymethoxy)- or bis(2-(benzyloxy)-substituted selenes of the general structure II.

Mono-protection of the Selenodiphenol

EXAMPLE 4

Synthesis of 2-((2-(benzyloxy)-3,5-dimethylphenyl)selanyl)-4,6-dimethylphenol IIc In a baked-out 25 ml Schlenk flask under an argon atmosphere, 40.2 mg (1.01 mmol, 1.0 eq, 60% in paraffin oil) of sodium hydride were suspended in 3.0 ml of abs. THF and cooled to 0° C. Subsequently, 324 mg (1.01 mmol, 1.0 eq) of selenodiphenol IIb, dissolved in 2.0 ml of abs. THF, were added dropwise. The yellowish solution was stirred at 0° C. for 15 minutes and at RT for two hours. Subsequently, at 0° C., 119 µl (172 mg, 1.01 mmol, 1.0 eq) of benzyl bromide were added and the mixture was stirred at 0° C. for 30 minutes. After a further 16 hours at RT, the solvent was removed under reduced pressure. 391 mg of the reaction mixture of 2-((2-(benzyloxy)-3,5-dimethylphenyl)selanyl)-4,6-dimethylphenol IIc (1b*) (314 mg, 0.762 mmol, 76%) and bis(2-(benzyloxy)-3,5-dimethylphenyl)selane IIc (1b) (76.6 mg, 0.152 mmol, 15%) in a ratio of 4.96:1 (determined from crude ¹H NMR spectrum) were obtained. By means of purification by column chromatography (100% H →100:1 →50:1 →20:1 →10:1 H/DCM) it was possible to obtain 51.0 mg of compound IIc (1b*), which was subsequently characterized as follows:

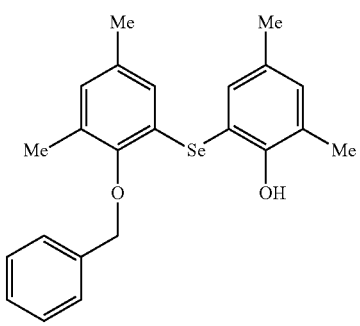 [SMILES: Cc1cc(C)c(O)c([Se]c2cc(C)cc(C)c2OCc2ccccc2)c1]

IR (ATR): $\hat{\upsilon}$ (cm$^{-1}$)=3409; 3030; 3011; 2919; 2854; 2730; 1567; 1497; 1467; 1372; 1328; 1284; 1268; 1251; 1231; 1208; 1123; 1078; 1010; 976; 912; 858; 814; 763; 749; 725; 695; 602; 570; 516; 491; 461; $^1$H-NMR (300 MHz, toluene-d$_8$): δ (ppm)=7.62-7.43 (m, 2H, Ar—CH); 7.36-7.29 (m, 1H, Ar—CH); 7.28-7.08 (m, 2H, Ar—CH); 6.86-6.66 (m, 3H, Ar—CH); 6.58 (d, J=2.1 Hz, 1H, Ar—CH); 4.82 (s, 2H, —OCH$_2$Ph); 2.27 (s, 3H, —CH$_3$); 2.12 (d, J=2.4 Hz, 3H, —CH$_3$); 2.07 (s, 3H, —CH$_3$); 1.86 (s, 3H, —CH$_3$); $^{13}$C-NMR (75 MHz, toluene-d$_8$): δ (ppm)=154.2; 153.2; 137.7; 136.0; 135.1; 134.6; 131.3; 131.2; 129.7; 129.0; 128.6; 128.3; 128.2; 128.1; 74.94; 30.30; 20.53; 20.18; 16.93; 16.31; $^{77}$Se-NMR (57 MHz, toluene-d$_8$): δ (ppm)=207.3; HR-MS (ESI-TOF): calc. for C$_{23}$H$_{25}$O$_2$Se ([M+H]$^+$): 413.10155, found: 413.10109; calc. for C$_{23}$H$_{24}$O$_2$SeNa ([M+Na]$^+$): 435.0835, found: 435.08378; C$_{23}$H$_{24}$O$_2$Se (412.09 g/mol).

The oxidation of diphenyl selenide IV under the conditions described is known from the literature; the other oxidations were conducted in an analogous manner.

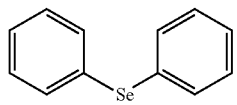
(IV)

Synthesis of the Organodiaryl Selenoxide Compounds

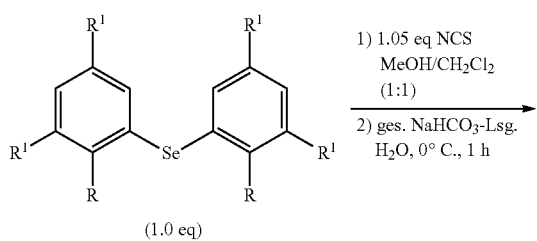

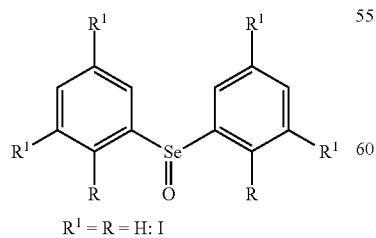

R$^1$ = R = H: I
R$^1$ = Me, R = OMOM: Ic (1a)
R$^1$ = Me, R = OBn: Ic (1b)

GP 2: In a 50 ml two-neck flask, 1.0 eq. of the organodiphenyl selenide II compound was dissolved in a 1:1 mixture of dichloromethane/methanol (13.4 ml/1.0 mmol) and cooled to 0° C. Subsequently, 1.05 eq. of N-chlorosuccinimide were added and the mixture was stirred at 0° C. for 30 minutes, in the course of which a pale yellow color of the solution was observed. Subsequently, a saturated NaHCO$_3$ solution (1.0 ml/1.0 mmol) was added, the mixture was stirred for 15 minutes, water (15 ml/1.0 mmol) was added and the mixture was stirred once again at 0° C. for 15 minutes. And the organic phase was washed with water (3×25 ml/1.0 mmol). The aqueous phase was extracted with dichloromethane (3×25 ml/1.0 mmol) and dried over magnesium sulphate. The desiccant was filtered off, the solvent was removed under reduced pressure and the crude product was dried under vacuum at 50° C. for three hours.

a) Synthesis of Seleninyldibenzene III (Comparative Example)

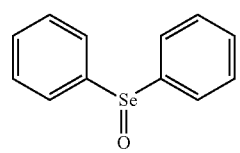
III

According to GP 2, 175 μl (234 mg, 1.00 mmol, 1.0 eq) of diphenyl selenide were reacted with 140 mg (1.05 mmol, 1.05 eq) of N-chlorosuccinimide. After extractive workup, 235 mg (0.940 mmol, 94%) of the title compound III were obtained as a colourless solid.

IR (ATR): $\hat{\upsilon}$ (cm$^{-1}$)=3044; 3008; 2989; 2941; 1570; 1470; 1437; 1300; 1156; 1069; 1056; 1047; 1017; 993; 915; 850; 820; 733; 686; 611; 481; 442, $^1$H NMR (300 MHz, toluene-d$_8$): δ (ppm)=7.67-7.51 (m, 4H, Ar—CH); 7.16-6.87 (m, 6H, Ar—CH); $^{13}$C NMR (75 MHz, toluene-d$_8$): δ (ppm)=145.1; 130.5; 129.3; 126.0; $^{77}$Se NMR (57 MHz, toluene-d$_8$): δ (ppm)=851.0; HR-MS (ESI-TOF): calc. for C$_{12}$H$_{11}$OSe ([M+H]$^+$): 250.99700, found: 250.99691; calc. for C$_{12}$H$_{10}$OSeNa ([M+Na]$^+$): 272.97894, found: 272.97888; C$_{12}$H$_{10}$OSe (249.99 g/mol). The analytical data are in agreement with the literature data.

b) 2-(Benzyloxy)-1-((2-(methoxymethoxy)-3,5-dimethylphenyl)seleninyl)-3,5-dimethylbenzene Ic (1a)

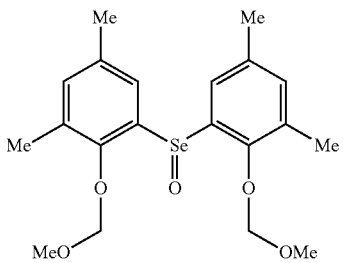 [SMILES: COCOc1c(C)cc(C)cc1[Se](=O)c1cc(C)cc(C)c1OCOC]

According to GP 2, 407 mg (0.991 mmol, 1.0 eq) of bis(2-(methoxymethoxy)-3,5-dimethylphenyl)selane IIc (1a) were reacted with 139 mg (1.04 mmol, 1.05 eq) of N-chlorosuccinimide. After extractive workup, 397 mg (0.932 mmol, 94%) of the title compound Ic (1a) were obtained as a colorless solid.

$^1$H NMR (300 MHz, dichloromethane-d$_2$): δ (ppm)=7.27-7.17 (m, 2H, Ar—CH); 7.12 (td, J=1.4, 0.7 Hz, 2H, Ar—CH); 5.02 (d, J=1.1 Hz, 4H, —OCH$_2$OCH$_3$); 3.59 (s, 6H, —OCH$_3$); 2.29 (d, J=0.7 Hz, 6H, 5-CH$_3$); 2.28 (t, J=0.6 Hz, 6H, 3-CH$_3$); $^{13}$C NMR (75 MHz, dichloromethane-d$_2$): δ (ppm)=152.3; 137.1; 135.7; 131.6; 125.6; 100.7; 58.14; 0.94; 16.84; $^{77}$Se NMR (57 MHz, toluene-d8): δ (ppm)=831.0 ppm; C$_{20}$H$_{26}$O$_5$Se (426.09 g/mol).

c) Synthesis of 6,6'-seleninylbis 1-(benzyloxy)-2,4-dimethylbenzene Ic (1b)

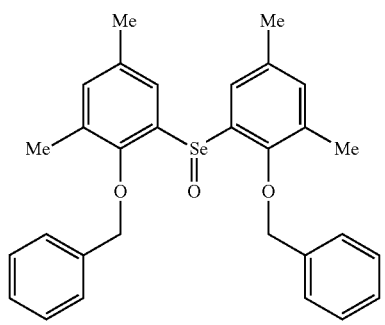 [SMILES: Cc1cc(C)c(OCc2ccccc2)c([Se](=O)c2cc(C)cc(C)c2OCc2ccccc2)c1]

According to GP 2, 185 mg (0.369 mmol, 1.0 eq) of bis(2-(benzyloxy)-3,5-dimethylphenyl)selane IIc (1b) were reacted with 51.7 mg (1.05 mmol, 1.05 eq) of N-chlorosuccinimide. After extractive workup, 143 mg (0.276 mmol, 75%) of the title compound Ic (1b) were obtained as a colorless solid.

IR (ATR): $\hat{υ}$ (cm$^{-1}$)=3376; 3089; 3062; 3031; 3004; 2953; 2920; 2853; 2734; 1588; 1467; 1374; 1364; 1270; 1233; 1219; 1207; 1196; 1116; 1080; 1041; 916; 863; 842; 824; 777; 748; 725; 696; 600; 567; 524; 514; 495; 464; $^1$H-NMR (300 MHz, toluene-d8): δ (ppm)=7.46 (d, J=2.2 Hz, 1H, Ar—CH); 7.12-7.03 (m, 4H, Ar—CH); 6.98-6.87 (m, 4H, Ar—CH); 6.83 (p, J=1.1 Hz, 1H, Ar—CH); 6.81-6.77 (m, 2H, Ar—CH); 6.49 (d, J=2.0 Hz, 2H, Ar—CH); 4.57 (d, J=11.2 Hz, 2H, —CHHPh); 4.39 (d, J=11.3 Hz, 2H—CHHPh); 1.79 (s, 6H, 5-CH$_3$); 1.75 (s, 6H, 3-CH$_3$); $^{13}$C-NMR (75 MHz, toluene-d$_8$): δ (ppm)=154.0; 138.0; 135.5; 135.0; 131.2; 128.4; 128.1; 127.9; 126.6; 125.6; 76.05; 20.58; 16.00; $^{77}$Se-NMR (57 MHz, toluene-d$_8$): δ (ppm)=834.2 ppm; HR-MS (ESI-TOF): calc. for C$_{30}$H$_{31}$O$_3$Se ([M+H]$^+$): 519.14351, found: 519.14372; calc. for C$_{30}$H$_{30}$O$_3$SeNa ([M+Na]$^+$): 541.12545, found: 541.12524; C$_{30}$H$_{30}$O$_3$Se (518.14 g/mol).

Catalysis—Hydroformylation

Scheme 1: Details of the substances tested in the rhodium-catalysed hydroformylation.

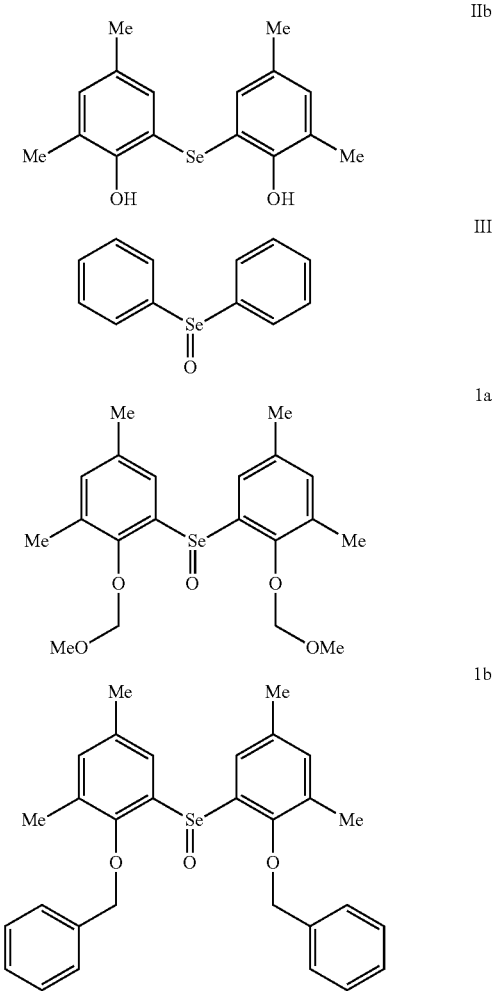

TABLE 1

Details of the catalysis experiments using noninventive organoselenium compounds

| Entry | Ligand | Olefin/solvent | Rh/ligand/olefin ratio | p [bar] | T [° C.] | t [h] | Y [%] | S [%] |
|---|---|---|---|---|---|---|---|---|
| 1 | IIb | n-octene/toluene | 1:1:2197 (100 ppm Rh) | 50 | 120 | 4 | 9.5 | 33.2 |
| 2 | III | n-octene/toluene | 1:1:2205 (40 ppm Rh) | 50 | 120 | 4 | 89.5 | 28.1 |
| 3* | 1a | n-octene/toluene | 1:1:2203 (100 ppm Rh) | 50 | 120 | 4 | 96.1 | 28.1 |
| 4* | 1b | n-octene/toluene | 1:1:2215 (100 ppm Rh) | 50 | 120 | 4 | 96.7 | 28.4 |

Notes for Table 1:
p = pressure, T = temperature, t = time, Y = yield; S = n-regioselectivity, *= inventive Rhodium-catalyzed hydroformylation with an unprotected selenodiphenol IIb (Entry 1) leads to a low yield of 9.5% (retention of 90.5% residual olefin) and an n-regioselectivity of 33.2%.

Catalysis experiment 2) illustrates the successful use of the unsubstituted diphenyl selenoxide compound in rhodium-catalysed hydroformylation.

Through use of the organodiphenyl selenoxide III, a high yield of 89.5% in hydroformylation with n-octene was recorded.

By comparison, it was possible to enhance the yields further in experiments 3) and 4), with the same good selectivity. The use of the inventive ligands 1a and 1b thus leads to a higher yield of product of value. A maximum yield is essential for the economic viability of processes on the industrial scale, since it is possible in this way to achieve the greatest possible creation of value from the raw materials.

The stated object was thus achieved using the inventive ligands 1a and 1b.

The invention claimed is:

1. An organodiaryl selenoxide compound of general structure (Ia)

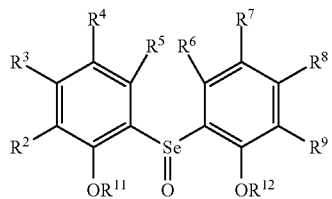

(Ia)

where $R^2$, $R^3$, $R^4$, $R^7$, $R^8$ and $R^9$ in structure (Ia) are each independently selected from the group consisting of: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —SO$_3$H, —CN, and —N[($C_1$-$C_{12}$)-alkyl]$_2$, where the alkyl and aryl groups are each independently unsubstituted or substituted, where substituted —($C_1$-$C_{12}$)-alkyl groups and substituted —($C_6$-$C_{20}$)-aryl groups have at least one substituent and the at least one substituent in each case is independently selected from the group consisting of —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl, and alkoxycarbonyl, where $R^5$ and $R^6$ in structure (Ia) are each independently selected from the group consisting of: —H, —($C_1$-$C_{12}$)-alkyl, —O—($C_2$-$C_{12}$)-alkyl, —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —SO$_3$H, —CN, and N[($C_1$-$C_{12}$)-alkyl]$_2$, where the alkyl and aryl groups are each independently unsubstituted or substituted, where substituted —($C_1$-$C_{12}$)-alkyl group and substituted —($C_6$-$C_{20}$)-aryl groups have at least one substituent and the at least one substituent is in each case independently selected from the group consisting of —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl, and alkoxycarbonyl, where —$R^{11}$ and —$R^{12}$ in each case in structure (Ia) are independently selected from the group consisting of: —H, —($C_1$-$C_{12}$)-alkyl, —($C_1$-$C_{12}$)-alkyl-O—($C_1$-$C_{12}$)-alkyl, —($C_6$-$C_{20}$)-aryl, —($C_1$-$C_{12}$)-alkyl-O—($C_8$-$C_{20}$)-aryl, —($C_6$-$C_{20}$)-aryl-O—($C_6$-$C_{20}$)-aryl, and —C=O—($C_1$-$C_{12}$)-alkyl, where the alkyl and aryl groups mentioned are each independently unsubstituted or substituted, where substituted —($C_1$-$C_{12}$)-alkyl groups and substituted —($C_8$-$C_{20}$)-aryl groups have at least one substituent and the at least one substituent is in each case independently selected from the group consisting of —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl, and alkoxycarbonyl.

2. The compound according to claim 1 of general structure (Ib)

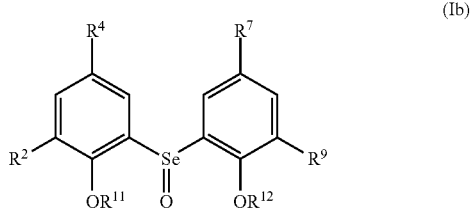

(Ib)

where $R^2$, $R^4$, $R^7$ and $R^9$ in structure (Ib) are —($C_1$-$C_{12}$)-alkyl, where —$R^{11}$ and —$R^{12}$ in structure (Ib) are each independently selected from the group consisting of: —H, —($C_1$-$C_{12}$)-alkyl, —($C_1$-$C_{12}$)-alkyl-O—($C_1$-$C_{12}$)-alkyl, —($C_6$-$C_{20}$)-aryl, —($C_1$-$C_{12}$)-alkyl-O—($C_6$-$C_{20}$)-aryl, —($C_6$-$C_{20}$)-aryl-O—($C_6$-$C_{20}$)-aryl, and —(C=O)—O—($C_1$-$C_{12}$)-alkyl, where the alkyl and aryl groups mentioned are each independently unsubstituted or substituted, where substituted —($C_1$-$C_{12}$)-alkyl groups and substituted —($C_6$-$C_{20}$)-aryl groups have at least one substituent and the at least one substituent in each case is independently selected from the group consisting of —($C_3$-$C_{12}$)-cycloalkyl, —($C_3$-$C_{12}$)-heterocycloalkyl, —($C_8$-$C_{20}$)-aryl, fluorine, chlorine, cyano, formyl, acyl, and alkoxycarbonyl.

3. The compound according to claim 1, wherein, in the organodiaryl selenoxide of the structures (Ia)

$R^2$, $R^3$, $R^4$, $R^7$, $R^8$ and $R^9$ are each independently selected from the group consisting of: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —SO$_3$H, —CN, and —N[($C_1$-$C_{12}$)-alkyl]$_2$, where the alkyl and aryl groups are each independently unsubstituted or substituted, where substituted —($C_1$-$C_{12}$)-alkyl groups and substituted —($C_6$-$C_{20}$)-aryl groups have at least one substituent and the at least one substituent in each case is independently selected from the group consisting of —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl, and alkoxycarbonyl, and at least one radical of $R^2$, $R^3$, $R^4$, $R^7$, $R^8$ and $R^9$ in each case is independently selected from the group consisting of: —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)- alkyl, —CO—(C₁-C₁₂)-alkyl, —CO—(C₆-C₂₀)-aryl, —SO₃H, —CN, and —N[(C₁-C₁₂)-alkyl]₂, where the alkyl and aryl groups are each independently unsubstituted or substituted, where substituted —(C₁-C₁₂)-alkyl groups and substituted —(C₆-C₂₀)-aryl groups have at least one substituent and the at least one substituent in each case is independently selected from the group consisting of —(C₃-C₁₂)-cycloalkyl, —(C₃-C₁₂)-heterocycloalkyl, —(C₆-C₂₀)-aryl, fluorine, chlorine, cyano, formyl, acyl, and alkoxycarbonyl.

4. The compound according to claim 1, wherein, in the organodiaryl selenoxide
   a) of the structure (Ia) or (Ib), R¹¹ is the same as R¹² and is selected from the group consisting of methoxymethyl-, benzyl-, and tert-butyl, or
   b) of the structure (Ia) or (Ib), R¹¹ is selected from the group consisting of methoxymethyl-, benzyl-, and tert-butyl, and R¹² is —H, or
   c) of the structure (Ia) or (Ib), R¹² is selected from the group consisting of methoxymethyl-, benzyl-, and tert-butyl, and R¹¹ is —H.

5. The compound according to claim 1, where R², R³, R⁴, R⁷, R⁸, R⁹ are each independently selected from the group consisting of: —H, —(C₁-C₁₂)-alkyl, —O—(C₁-C₁₂)-alkyl, —(C₆-C₂₀)-aryl, and —O—(C₆-C₂₀)-aryl.

6. The compound according to claim 1, where R⁵ and R⁶ are each independently selected from the group consisting of: —H, —(C₁-C₁₂)-alkyl, —O—(C₂-C₁₂)-alkyl, —(C₆-C₂₀)-aryl, and —O—(C₆-C₂₀)-aryl.

7. The compound according to claim 1, where R², R⁴, R⁷ and R⁹ are each independently selected from the group consisting of: —(C₁-C₁₂)-alkyl, —O—(C₁-C₁₂)-alkyl, —(C₆-C₂₀)-aryl, and —O—(C₆-C₂₀)-aryl.

8. The compound according to claim 1, where R², R⁴, R⁷, R⁹ are each methyl- or tert-butyl- and R³, R⁵, R⁶, R⁸ are each —H.

9. A process for preparing an organodiaryl selenoxide of the general structure (Ia), comprising the process step of
   (i) oxidizing an organodiaryl selenide of the general structure (IIa)

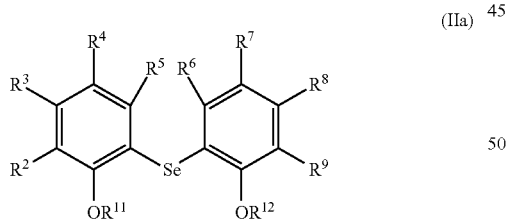

(IIa)

where R², R³, R⁴, R⁷, R⁸ and R⁹ in structure (Ia) are each independently selected from the group consisting of: —H, —(C₁-C₁₂)-alkyl, —O—(C₁-C₁₂)-alkyl, —(C₆-C₂₀)-aryl, —O—(C₆-C₂₀)-aryl, -halogen, —OC═O—(C₁-C₁₂)-alkyl, —S-alkyl, —S-aryl, —COO—(C₁-C₁₂)-alkyl, —CONH—(C₁-C₁₂)-alkyl, —CO—(C₁-C₁₂)-alkyl, —CO—(C₆-C₂₀)-aryl, —SO₃H, —CN, and —N[(C₁-C₁₂)-alkyl]₂, where the alkyl and aryl groups are each independently unsubstituted or substituted, where substituted —(C₁-C₁₂)-alkyl groups and substituted —(C₆-C₂₀)-aryl groups have at least one substituent and the at least one substituent in each case is independently selected from the group consisting of —(C₃-C₁₂)-cycloalkyl, —(C₃-C₁₂)-heterocycloalkyl, —(C₆-C₂₀)-aryl, fluorine, chlorine, cyano, formyl, acyl, and alkoxycarbonyl, where R⁵ and R⁶ in structure (Ia) are each independently selected from the group consisting of: —H, —(C₁-C₁₂)-alkyl, —O—(C₂-C₁₂)-Alkyl, —(C₆-C₂₀)-aryl, —O—(C₆-C₂₀)-aryl, -halogen, —OC═O—(C₁-C₁₂)-alkyl, —S-alkyl, —S-aryl, —COO—(C₁-C₁₂)-alkyl, —CONH—(C₁-C₁₂)-alkyl, —CO—(C₁-C₁₂)-alkyl, —CO—(C₆-C₂₀)-aryl, —COOH, —SO₃H, —CN, and —N[(C₁-C₁₂)-alkyl]₂, where the alkyl and aryl groups are each independently unsubstituted or substituted, where substituted —(C₁-C₁₂)-alkyl groups and substituted —(C₆-C₂₀)-aryl groups have at least one substituent and the at least one substituent in each case is independently selected from the group consisting of —(C₃-C₁₂)-cycloalkyl, —(C₃-C₁₂)-heterocycloalkyl, —(C₆-C₂₀)-aryl, fluorine, chlorine, cyano, formyl, acyl, and alkoxycarbonyl, where —R¹¹ and —R¹² in each case in structure (Ia) are independently selected from the group consisting of: —H, —(C₁-C₁₂)-alkyl, —(C₁-C₁₂)-alkyl-O—(C₁-C₁₂)-Alkyl, —(C₆-C₂₀)-aryl, —(C₁-C₁₂)-alkyl-O—(C₆-C₂₀)-aryl, —(C₆-C₂₀)-aryl-O—(C₆-C₂₀)-aryl, and —C═O—(C₁-C₁₂)-alkyl, where the alkyl and aryl groups mentioned are each independently unsubstituted or substituted, where substituted —(C₁-C₁₂)-alkyl groups and substituted —(C₆-C₂₀)-aryl groups have at least one substituent and the at least one substituent in each case is independently selected from the group consisting of —(C₃-C₁₂)-cycloalkyl, —(C₃-C₁₂)-heterocycloalkyl, —(C₆-C₂₀)-aryl, fluorine, chlorine, cyano, formyl, acyl, and alkoxycarbonyl, (ii) at least one compound of an organodiaryl selenoxide of the general structure (Ia) is obtained

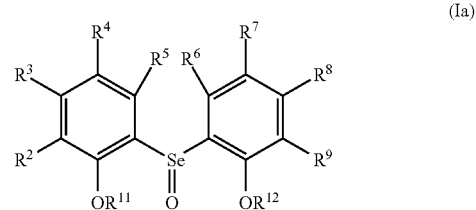

(Ia)

where R², R³, R⁴, R⁷, R⁸ and R⁹ in structure (Ia) are each independently selected from the group consisting of: —H, —(C₁-C₁₂)-alkyl, —O—(C₁-C₁₂)-alkyl, —(C₆-C₂₀)-aryl, —O—(C₆-C₂₀)-aryl, -halogen, —OC═O—(C₁-C₁₂)-alkyl, —S-alkyl, —S-aryl, —COO—(C₁-C₁₂)-alkyl, —CONH—(C₁-C₁₂)-alkyl, —CO—(C₁-C₁₂)-alkyl, —CO—(C₆-C₂₀)-aryl, —SO₃H, —CN, and N[(C₁-C₁₂)-alkyl]₂, where the alkyl and aryl groups are each independently unsubstituted or substituted, where substituted —(C₁-C₁₂)-alkyl group and substituted —(C₆-C₂₀)-aryl groups have at least one substituent and the at least one substituent is in each case independently selected from the group consisting of —(C₃-C₁₂)-cycloalkyl, —(C₃-C₁₂)-heterocycloalkyl, —(C₆-C₂₀)-aryl, fluorine, chlorine, cyano, formyl, acyl, and alkoxycarbonyl, where $R^5$ and $R^6$ in structure (Ia) are each independently selected from the group consisting of: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3H$, —CN, and N[($C_1$-$C_{12}$)-alkyl]$_2$, where the alkyl and aryl groups are each independently unsubstituted or substituted, where substituted —($C_1$-$C_{12}$)-alkyl group and substituted —($C_6$-$C_{20}$)-aryl groups have at least one substituent and the at least one substituent is in each case independently selected from the group consisting of —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl, and alkoxycarbonyl, where —$R^{11}$ and —$R^{12}$ in structure (Ia) are each independently selected from the group consisting of: —H, —($C_1$-$C_{12}$)-alkyl, —($C_1$-$C_{12}$)-alkyl-O—($C_1$-$C_{12}$)-alkyl, —($C_6$-$C_{20}$)-aryl, —($C_1$-$C_{12}$)-alkyl-O—($C_6$-$C_{20}$)-aryl, —($C_6$-$C_{20}$)-aryl-O—($C_6$-$C_{20}$)-aryl, and —(C=O)—O—($C_1$-$C_{12}$)-alkyl, where the alkyl and aryl groups mentioned are each independently unsubstituted or substituted, where substituted —($C_1$-$C_{12}$)-alkyl groups and substituted —($C_6$-$C_{20}$)-aryl groups have at least one substituent and the at least one substituent in each case is independently selected from the group consisting of —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl, and alkoxycarbonyl.

10. The process according to claim 9,
wherein (i) the oxidizing agent for oxidation of the organodiaryl selenide of the general structure (II) comprises N-chlorosuccinimide (CNS), bromosuccinimide (BNS), hydrogen peroxide, tert-butyl hypochlorite (tBuOCl), sodium hypochlorite (NaOCl) and/or meta-chlorobenzoic acid (mCPBA).

11. A complex comprising
at least one organodiaryl selenoxide of claim 1 and
at least one metal atom selected from the group consisting of Rh, Ru, Co, and Ir.

12. A process comprising the process steps of
(i) initially charging at least one olefin,
(ii) adding a complex according to claim 11,
and a substance including a metal atom selected from the group consisting of: Rh, Ru, Co, and Ir,
(iii) feeding in $H_2$ and CO,
(iv) heating the reaction mixture,
wherein the olefin is converted to an aldehyde.

13. A process comprising the process steps of
(i) initially charging at least one olefin,
(ii) adding an organodiaryl selenoxide according to claim 1 and a substance including a metal atom selected from the group consisting of: Rh, Ru, Co, and Ir,
(iii) feeding in $H_2$ and CO,
(iv) heating the reaction mixture,
wherein the olefin is converted to an aldehyde.

* * * * *